United States Patent [19]
Gonzenbach et al.

[11] Patent Number: 5,985,251
[45] Date of Patent: Nov. 16, 1999

[54] LIGHT SCREENING COMPOSITIONS

[75] Inventors: Hans Ulrich Gonzenbach, Geneva; Alain Bringhen, Croix-de-Rozon, both of Switzerland; Dominique Sidrac, Saint Julien, France

[73] Assignee: Roche Vitamins Inc., Parsippany, N.J.

[21] Appl. No.: 09/195,110

[22] Filed: Nov. 18, 1998

[30] Foreign Application Priority Data

Dec. 1, 1997 [EP] European Pat. Off. .............. 97121090

[51] Int. Cl.$^6$ .............................. A61K 7/42; A61K 7/44; A61K 7/00
[52] U.S. Cl. .............................. 424/59; 424/60; 424/400; 424/401
[58] Field of Search .............................. 424/59, 60, 400, 424/401

[56] References Cited

U.S. PATENT DOCUMENTS

| | | | |
|---|---|---|---|
| 4,387,089 | 6/1983 | De Polo | 424/59 |
| 4,726,942 | 2/1988 | Lang et al. | 424/47 |
| 5,403,944 | 4/1995 | Frater et al. | 556/441 |
| 5,576,354 | 11/1996 | Deflandre et al. | 514/685 |
| 5,605,678 | 2/1997 | Ascione et al. | 424/59 |
| 5,605,680 | 2/1997 | Deflandre et al. | 424/59 |
| 5,786,475 | 7/1998 | Fuso et al. | 544/198 |

FOREIGN PATENT DOCUMENTS

| | | |
|---|---|---|
| 0514 491 B1 | 11/1992 | European Pat. Off. . |
| 0538 431 B1 | 4/1993 | European Pat. Off. . |
| 0693 483 A1 | 1/1996 | European Pat. Off. . |
| 0704 437 A2 | 4/1996 | European Pat. Off. . |
| 0704 444 A1 | 4/1996 | European Pat. Off. . |
| 0780 119 A1 | 6/1997 | European Pat. Off. . |
| 0780 382 A1 | 6/1997 | European Pat. Off. . |

OTHER PUBLICATIONS

Klein, "Encyclopeidia of UV Absorbers for Sunscreen Products", Cosmetics & Toiletries, vol. 107, pp. 45–50 (1992).
Finkel, "Formulierung Kosmetischer Sonnenschutzmittel", SOeFW Journal, vol. 122, No. 8, pp. 543–546 and 548 (1996).

Primary Examiner—Shelley A. Dodson
Attorney, Agent, or Firm—George W. Johnston; Dennis P. Tramaloni; Eileen M. Ebel

[57] ABSTRACT

The invention relates to cosmetic light-screening compositions comprising at least one fatty phase and a) about 0.5 to 5 wt % of a dibenzoylmethane derivative, preferably about 0.5 to 3 wt %;
b) about 0.5 to 12 wt % of a 3,3-diphenylacrylate- or benzylidene camphor derivative, preferably about 0.5 to 10 wt %; and
c) about 1 to 15 wt % of a water-soluble p-methoxycinnamate derivative, preferably about 1 to 10 wt %.

20 Claims, No Drawings

LIGHT SCREENING COMPOSITIONS

FIELD OF THE INVENTION

The invention relates to photostable, cosmetic light-screening compositions for the protection of the human epidermis and the hairs against the ultraviolet rays of wavelengths between 280 and 320 (UV-B) and 320 and 400 nm (UV-A).

In particular, the invention relates to cosmetic light-screening compositions containing a dibenzoylmethane derivative as UV-A screening agent, a 3,3-diphenylacrylate derivative or a benzylidene camphor derivative as stabilizing agent and a water-soluble p-methoxycinnamate derivative as UV-B screening agent.

BACKGROUND OF THE INVENTION

Dibenzoylmethane derivatives such as 4-tert-butyl-4'-methoxy-dibenzoylmethane (PARSOL 1789) absorb UV-A radiation quite significantly and effectively up to 380 nm. However, no UV-A blocking sunscreen can be used alone if absorbtion in a wide band of UV-radiation is required. Thus, UV-A filters usually must be combined with an UV-B absorbing agent. Most popular is the combination of 4-tert-butyl-4'-methoxy-dibenzoylmethane with 2-ethylhexyl-p-methoxycinnamate (PARSOL MCX). Such a combination is described in U.S. Pat. No. 4,387,089. Many customary preparations contain a combination of PARSOL 1789 and PARSOL MCX.

As dibenzoylmethane derivatives are photolabile it is necessary to photostabilise these UV-A filters.

Cosmetic light-screening compositions based on dibenzoylmethane derivatives as UV-A filter and photostabilised with 3,3-diphenylacrylate derivatives are described in the European patent publication EP-0 514 491 B1. Said known compositions comprise at least one fatty phase, 1–5 wt % of a dibenzoylmethane derivative and at least 1 wt % of a 3,3-diphenylacrylate derivative. The mole ratio of the 3,3-diphenylacrylate derivative to the dibenzoylmethane derivative is not less than 0.8 and not more than 8. Said light-screening compositions may contain, in addition, water soluble LV-B screening agents like 2-phenyl-benzimidazole-5-sulfonic acid (PARSOL HS), terephthalydene-3-3'-dicamphor-10,10'-disulfonic acid (MEXORYL SX) and water-soluble UV-A screening agents like 2-hydroxy-4-methoxy-benzophenone-5-sulfonic acid, (UNIVUL MS-40). However, cinnamic acid derivatives are not mentioned.

The European patent publication EP 0 780 119 A1 describes a photostable, cosmetic light-screening composition comprising at least one fatty phase, 0.1–5 wt % of a dibenzoylmethane derivative and 0.5–4.5 wt % of a 3,3-diphenylacrylate derivative as stabilizer. The mole ratio of the 3,3-diphenylacrylate derivative to the dibenzoylmethane derivative is less than 0.8. Said light-screening compositions may contain, in addition, polysiloxane derivatives, polyacrylate derivatives or microfine metal oxides as UV-B filters. However, cinnamic acid derivatives are not mentioned.

Cosmetic light-screening compositions based on dibenzoylmethane derivatives as UV-A filter and photostabilised with benzylidene camphor derivatives are described in U.S. Pat. No. 5,605,680. Said known compositions comprise at least one fatty phase, 1–3 wt % of 4-tert-butyl-4'-methoxy-dibenzoylmethane and at least 4.5 wt % of p-methylbenzylidene camphor. The weight ratio of the p-methylbenzylidene camphor to the 4-tert-butyl-4'-methoxy-dibenzoylmethane is greater or equal to 3. Additional UV-A or UV-B filters are not mentioned in this patent publication.

A large number of popular broadband light screening compositions are based on PARSOL MCX and PARSOL 1789 as essential UV-B and respectively, UV-A filters. Additional UV filters are optional. In many such cases, the stabilisation of PARSOL 1789 by octocrylene as suggested in the above mentioned European patent publications EP-0 514 491B1 and EP-0 780 119 A1 is not sufficient. The stabilisation of PARSOL 1789 by p-methyl-benzylidene camphor as suggested in the above mentioned U.S. Pat. No. 5,605,680 is also not sufficient.

It has now been found that a light screening composition comprising a dibenzoylmethane derivative as UV-A filter, a water-soluble p-methoxy-cinnamate derivative as UV-B filter and a 3,3-diphenylacrylate derivative or a benzylidene camphor derivative as stabilizer shows a surprisingly higher photostability compared to a corresponding light screening composition containing the commonly used PARSOL MCX as UV-B filter.

SUMMARY OF THE INVENTION

Accordingly, the present invention is concerned with a photostable cosmetic light-screening composition comprising, at least one fatty phase, a) from about 0.5 to about 5 wt % of a dibenzoylmethane derivative;

b) from about 0.5 to about 12 wt % of a 3,3-diphenylacrylate derivative or a benzylidene camphor derivative; and c) from about 1 to about 15 wt % of a water-soluble p-methoxycinnamate derivative.

Preferably, the dibenzoylmethane derivative is present in an amount of from about 0.5 to 3 wt %; the 3,3-diphenylacrylate derivative or the benzylidene camphor derivative is present in an amount of from about 0.5 to 10 wt %; and the water-soluble p-methoxycinnamate derivative is present in an amount of from about 1 to about 10 wt %.

As preferred derivatives, 4-tert.-butyl-4'-methoxydibenzoylmethane is the preferred dibenzoylmethane derivative; 2-ethylhexyl-2-cyano-3,3-diphenylacrylate (octocrylene) is the preferred 3,3-diphenylacrylate derivative; p-methylbenzylidene camphor is the preferred benzylidene camphor derivative; and the preferred water-soluble p-methoxycinnamate derivative is selected from the mono-, di-, or triethanolamine salt of p-methoxycinnamic acid.

DETAILED DESCRIPTION OF THE INVENTION

The present invention is concerned with a cosmetic light-screening composition comprising at least one fatty phase and a) from about 0.5 to about 5 wt % of a dibenzoylmethane derivative;

b) from about 0.5 to about 12 wt % of a 3,3-diphenylacrylate derivative or a benzylidene camphor derivative; and c) from about 1 to about 15 wt % of a water-soluble p-methoxycinnamate derivative.

Preferably, the dibenzoylmethane derivative is present in an amount of from about 0.5 to 3 wt %; the 3,3-diphenylacrylate derivative or the benzylidene camphor derivative is present in an amount of from about 0.5 to 10 wt %; and the water-soluble p-methoxycinnamate derivative is present in an amount of from about 1 to about 10 wt %.

As preferred derivatives, 4-tert.-butyl-4'-methoxydibenzoylmethane is the preferred dibenzoylmethane derivative; 2-ethylhexyl-2-cyano-3,3-diphenylacrylate (octocrylene) is the preferred 3,3-diphenylacrylate derivative; p-methylbenzylidene camphor is the preferred benzylidene camphor derivative; and the preferred water-soluble p-methoxycinnamate derivative is selected from the mono-, di-, or triethanolamine salt of p-methoxycinnamic acid.

The term "dibenzoylmethane derivative" refers in the present context to compounds such as e.g. 4-tert-butyl-4'-methoxy-dibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane and 2,6-dimethyl-4-tert-butyl-4'-methoxy-dibenzoylmethane. Preferred is 4-tert-butyl-4'-methoxy-dibenzoylmethane (PARSOL 1789).

The term "3,3-diphenylacrylate derivative" refers in the present context to compounds such as e.g. 2-ethylhexyl-2-cyano-3,3-diphenylacrylate (octocrylene) and 2-ethyl-2-cyano-3,3-diphenylacrylate (etocrylene). Preferred is octocrylene.

The term "benzylidene camphor derivative" refers in the present context preferably to p-methylbenzylidene camphor (PARSOL 5000).

The term "water-soluble p-methoxycinnamate derivative" refers in the present context to compounds such as e.g. ammonium-, sodium-, potassium-p-methoxycinnamate, salts of primary, secondary or tertiary amines of p-methoxycinnamic acid like mono-, di- or triethanol amine salts, aminomethyl-propanol salt, morpholine salt and the like. Preferred are mono-, di-, and triethanolamine salts.

The mole or weight ratio of the dibenzoylmethane derivative to the water-soluble p-methoxycinnamate derivative and of the dibenzoylmethane derivative to the 3,3-diphenylacrylate- or to the benzylidene camphor derivative is not critical. The following concentrations are preferred:

a) about 1 to 3 wt % of a dibenzoylmethane derivative;
b) about 0.5 to 10 wt % of a 3,3-diphenylacrylate- or benzylidene camphor derivative; and
c) about 1 to 10 wt % of a water-soluble p-methoxycinnamate derivative.

The dibenzoylmethane derivative used as UV-A filter and the 3,3-diphenylacrylate derivative used as stabilizer are both lipophilic. Thus, the cosmetic light screening composition contains at least one fatty phase and can consequently present themselves in the form of emulsions, lotions or gels.

The cosmetic bases which are conventional for light screening compositions in the scope of the present invention can be any customary preparation which complies with the cosmetic requirements e.g. in form of an oil, a lotion, a cream, a milk, a gel, a solid stick, an aerosol, a spray, a foam, a powder, a shampoo, a hair conditioner, a lacquer or a make-up, and the like.

Usual basic compounds known to the skilled practitioner can be used for the preparation of these forms, e.g. oils, waxes, alcohols, polyols, and the like. Preferred compounds are fatty acids, fatty acid esters, fatty alcohols, but also ethanol, isopropanol, propylene glycol, glycerine and the like.

The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments and the like.

In case of protection of the hairs, the suitable formulations are shampoos, conditioners, lotions, gels, emulsions, dispersions, lacquers, and the like.

Furthermore, monomeric or polymeric UV filter(s) can be added.

Suitable UV-B filters, i.e. substances having absorption maxima between about 290 and 320 nm, are for example the following organic compounds which belong to the widest classes of substance:

p-Aminobenzoic acid derivatives such as ethyl-, propyl-, butyl-, and isobutyl p-aminobenzoate and the like;

Acrylates such as 2-ethylhexyl-2-cyano-3,3-diphenylacrylate (octocrylene), ethyl 2-cyano-3,3-diphenylacrylate and the like;

Aniline derivatives such as methyl anilinum methosulfate and the like;

Anthranilic acid derivatives such as menthyl anthranilate and the like;

Benzophenone derivatives such as benzophenone-3, benzophenone-4 and the like.

Camphor derivatives such as methyl benzylidene camphor and the like;

Cinnamate derivatives such as octyl methoxycinnamate or ethoxyethyl methoxycinnamate and the like as well as cinnamic acid derivatives bond to siloxanes;

Gallic acid such as digalloyl trioleate and the like;

Imidazole derivatives such as phenyl benzimidazole sulfonic acid and the like;

Salicylate derivatives such as octyl salicylate, homomenthyl salicylate and the like;

Triazole derivatives such as hydroxyphenylbenztriazole and the like;

Triazone derivatives such as octyl triazone and the like; and

Pigments such as microparticulated $TiO_2$, ZnO and the like.

Suitable polymeric filters are polysiloxanes as described in the European patent publication EP 538431 B1.

The composition may further contain UV-A filters such as Triazine compounds as described in the European Patent Publications EP 0693483 A1, EP 0704437 A2, EP 0704444 A1 and EP 0780382 A1.

The preparation of all these formulations is well known to the skilled artisan in this field.

As described in the European patent publication EP 0 780 119 A1 there are cases where it is required to use the stabilizer in smaller dosages than the dosage of the UV-A filter used. Thus, the preferred mole ratio of the 3,3-diphenylacrylate derivative to the dibenzoylmethane derivative is less than 0.8 and the preferred weight ratio of p-methylbenzylidene camphor to the dibenzoylmethane derivative is less than 3.

The following Examples illustrate the light screen agents provided by the present invention.

In these Examples the abbreviations and trade names selected have the following significance:

| | |
|---|---|
| PARSOL 1789 | 4-tert.butyl-4'-methoxy-dibenzoylmethane sold under the trade name PARSOL 1789 by Roche. |
| PARSOL MCX | 2-ethylhexyl-p-methoxycinnamate sold under the trade name PARSOL MCX by Roche. |
| PARSOL Hydro | Diethanolamine salt of p-methoxycinnamic acid sold under the trade name PARSOL Hydro by Roche. |

| | |
|---|---|
| PARSOL 5000 | p-methylbenzylidene camphor sold under the trade name PARSOL 5000 by Roche. |
| UNIVUL N-539 | 2-Ethylhexyl-2-cyano-3,3-diphenylacrylate (octocrylene) sold under the trade name UNIVUL N-539 by BASF. |
| CETIOL LC: | Coco-caprilate-caprate sold under the trade name CETIOL LC by Henkel. |
| GANEX V 220 | Polyvinyl pyrrolidone/eicosene copolymer sold under the trade name GANEX V 220 by ISP. |
| MIGLYOL 812 N | Caprilic capric triglyceride sold under the trade name MIGLYOL 812 N by Hüls. |
| BHT | Butylhydroxytoluol (2,6 di-tert-butyl-4-methyl phenol). |
| EDTA | Disodium salt of ethylenediaminetetraacetic acid. |
| PHENONIP | Mixture of 4-hydroxy benzoic acid esters sold under the trade name PHENONIP by NIPA Ltd. |
| LANETTE O | Cetearyl alcohol sold under the trade name LANETTE O by Henkel. |
| CUTINA E 24 | Glyceryl stearate sold under the trade name CUTINA E 24 by Henkel. |
| CARBOPOL 981 | Carbomer 981 (1% dispersion in water, homopolymer of 10.0% acrylic acid crosslinked with an allyl ether of sucrose) sold under the trade name CARBOPOL 981 by B. F. Goodrich. |
| ARLAMOL E | POP-(15)-stearyl alcohol sold by ICI. |
| ARLAMOL HD | Heptamethylnonane sold by ICI. |
| BRIJ 72 | POE-(2)-stearyl alcohol sold by ICI. |
| BRIJ 721 | POE-(21)-stearyl alcohol sold by ICI. |
| ARLACEL P135 | PEG-30 dipolyhydroxystearate sold by ICI. |
| Stearic acid | Stearic acid sold by Unichema. |
| Silbione oil 70047 V20 | cyclomethicone sold by RhÙne Poulenc. |
| Keltrol | Xanthan gum sold by Kelco. |
| Propylene glycol | 1,2 propanediol sold by BASF. |
| Umordant P | water, sodium lactate, sodium PCA, urea, hydrolysed vegetable protein and asparagus extract and sodium phosphate sold by Cosmetochem. |

The salts of p-methoxycinnamic acid described in the Examples 3A, 3B, 4, 5, 6, 7, 8A, 8B, 10A–C, 11, 12, 13B, 13C were prepared by mixing p-methoxy-cinnamic acid with the appropriate base in an adequat solvent and purified by crystallization.

Examples 1A and 1B are comparative examples containing octocrylene as stabilizer and PARSOL MCX as UV-B filter instead of water-soluble p-methoxy-cinnamate.

Example 1C is a comparative example containing PARSOL 5000 as stabilizer and PARSOL MCX as UV-B filter instead of water-soluble p-methoxy-innamate.

Examples 2–8 refer to compounds according to the invention containing otocrylene as stabilizer.

Examples 9–13 refer to compounds according to the invention containing PARSOL 5000 as stabilizer.

Example 14 shows the photostability data.

EXAMPLES 1A and 1B (Comparative Examples)

Sunscreen lotion containing different amounts of PARSOL MCX and UNIVUL N-539 as shown in the following table:

| ingredients in % w/w | 1A a | 1A b | 1A c | 1A d | 1A e | 1A f |
|---|---|---|---|---|---|---|
| 1 PARSOL 1789 | 2.5 | 2.5 | 2.5 | 2.5 | 2.5 | 2.5 |
| 2 Glyceryl mono myristate | 4.0 | 4.0 | 4.0 | 4.0 | 4.0 | 4.0 |
| 3 CETIOL LC | 5.0 | 5.0 | 5.0 | 5.0 | 5.0 | 5.0 |
| 4 GANEX V 220 | 2.0 | 2.0 | 2.0 | 2.0 | 2.0 | 2.0 |
| 5 Cetylalcohol | 2.0 | 2.0 | 2.0 | 2.0 | 2.0 | 2.0 |
| 6 MIGLYOL 812 N | 10.0 | 10.0 | 10.0 | 10.0 | 10.0 | 10.0 |
| 7 BHT | 0.1 | 0.1 | 0.1 | 0.1 | 0.1 | 0.1 |
| 8 PHENONIP | 0.6 | 0.6 | 0.6 | 0.6 | 0.6 | 0.6 |
| 9 PARSOL MCX | 8.0 | 8.0 | 8.0 | 4.0 | 4.0 | 4.0 |
| 10 UNIVUL N-539 | 2.0 | 5.0 | 8.0 | 2.0 | 5.0 | 8.0 |
| 11 LANETTE O | 5.0 | 5.0 | 5.0 | 5.0 | 5.0 | 5.0 |
| 12 CUTINA E 24 | 4.0 | 4.0 | 4.0 | 4.0 | 4.0 | 4.0 |
| 13 Propylene glycol | 10.0 | 10.0 | 10.0 | 10.0 | 10.0 | 10.0 |
| 14 EDTA | 0.1 | 0.1 | 0.1 | 0.1 | 0.1 | 0.1 |
| 15 CARBOPOL 981 (1% sol) | 10.0 | 10.0 | 10.0 | 10.0 | 10.0 | 10.0 |
| 16 Demineralised water | 100 | 100 | 100 | 100 | 100 | 100 |
| 17 KOH to pH | 7 | 7 | 7 | 7 | 7 | 7 |

Procedure: The ingredients 1 to 12 are heated to 85° C. while stirring. When homogeneous ingredients 13 to 16, preheated to 75° C. are added while mixing. The mixture is cooled to 40° C. The pH-value is corrected to 7 with KOH. The water loss was compensated and the mixture was cooled to ambient temperature under stirring.

EXAMPLE 1B (Comparative Example)

| Ingredients in % w/w | 1B a | 1B b | 1B c | 1B d | 1B e | 1B f |
|---|---|---|---|---|---|---|
| 1 PARSOL MCX | 8.0 | 8.0 | 8.0 | 4.0 | 4.0 | 4.0 |
| 2 PARSOL 1789 | 2.5 | 2.5 | 2.5 | 2.5 | 2.5 | 2.5 |
| 3 UNIVUL N 539 | 8.0 | 5.0 | 2.0 | 8.0 | 5.0 | 2.0 |
| 4 Arlamol E | 5.0 | 5.0 | 5.0 | 5.0 | 5.0 | 5.0 |
| 5 Arlamol HD | 5.0 | 5.0 | 5.0 | 5.0 | 5.0 | 5.0 |
| 6 Brij 72 | 3.0 | 3.0 | 3.0 | 3.0 | 3.0 | 3.0 |
| 7 Brij 721 | 2.0 | 2.0 | 2.0 | 2.0 | 2.0 | 2.0 |
| 8 Arlacel P135 | 0.5 | 0.5 | 0.5 | 0.5 | 0.5 | 0.5 |
| 9 Lanette O | 5.0 | 5.0 | 5.0 | 5.0 | 5.0 | 5.0 |
| 10 Stearic Acid | 1.5 | 1.5 | 1.5 | 1.5 | 1.5 | 1.5 |
| 11 Silbione Oil 70047V20 | 1.0 | 1.0 | 1.0 | 1.0 | 1.0 | 1.0 |
| 12 BHT | 0.1 | 0.1 | 0.1 | 0.1 | 0.1 | 0.1 |
| 13 Phenonip | 0.6 | 0.6 | 0.6 | 0.6 | 0.6 | 0.6 |
| 14 Keltrol 1% sol'n | 12.0 | 12.0 | 12.0 | 12.0 | 12.0 | 12.0 |
| 15 Propylene Glycol | 4.0 | 4.0 | 4.0 | 4.0 | 4.0 | 4.0 |
| 16 Umordan P | 1.0 | 1.0 | 1.0 | 1.0 | 1.0 | 1.0 |
| 17 Deionized Water qsp | 100 | 100 | 100 | 100 | 100 | 100 |

Procedure: The ingredients 1 to 13 were heated to 85° C. while stirring. When homogeneous ingredients 14 to 17 were preheated to 75° C. The water loss was compensated and the mixture was cooled to the ambient temperature while stirring.

EXAMPLE 1C (Comparative Example)

Sunscreen emulsion according to the present invention containing different amounts of PARSOL MCX and PARSOL 5000 as shown in the following table:

| ingredients in % w/w | 1C a | 1C b | 1C c | 1C d | 1C e | 1C f |
|---|---|---|---|---|---|---|
| 1 PARSOL MCX | 8.0 | 8.0 | 8.0 | 4.0 | 4.0 | 4.0 |
| 2 PARSOL 1789 | 2.5 | 2.5 | 2.5 | 2.5 | 2.5 | 2.5 |
| 3 PARSOL 5000 | 8.0 | 5.0 | 2.0 | 8.0 | 5.0 | 2.0 |
| 4 Arlamol E | 5.0 | 5.0 | 5.0 | 5.0 | 5.0 | 5.0 |
| 5 Arlamol HD | 5.0 | 5.0 | 5.0 | 5.0 | 5.0 | 5.0 |
| 6 Brij 72 | 3.0 | 3.0 | 3.0 | 3.0 | 3.0 | 3.0 |
| 7 Brij 721 | 2.0 | 2.0 | 2.0 | 2.0 | 2.0 | 2.0 |
| 8 Arlacel P135 | 0.5 | 0.5 | 0.5 | 0.5 | 0.5 | 0.5 |
| 9 Lanette O | 5.0 | 5.0 | 5.0 | 5.0 | 5.0 | 5.0 |
| 10 Stearic Acid | 1.5 | 1.5 | 1.5 | 1.5 | 1.5 | 1.5 |
| 11 Silbione Oil 70047V20 | 1.0 | 1.0 | 1.0 | 1.0 | 1.0 | 1.0 |
| 12 BHT | 0.1 | 0.1 | 0.1 | 0.1 | 0.1 | 0.1 |
| 13 Phenonip | 0.6 | 0.6 | 0.6 | 0.6 | 0.6 | 0.6 |
| 14 Keltrol 1% sol'n | 12.0 | 12.0 | 12.0 | 12.0 | 12.0 | 12.0 |
| 15 Propylene Glycol | 4.0 | 4.0 | 4.0 | 4.0 | 4.0 | 4.0 |

-continued

| ingredients in % w/w | 1C a | 1C b | 1C c | 1C d | 1C e | 1C f |
|---|---|---|---|---|---|---|
| 16 Umordan P | 1.0 | 1.0 | 1.0 | 1.0 | 1.0 | 1.0 |
| 17 Deionized Water qsp | 100 | 100 | 100 | 100 | 100 | 100 |

Preparation according to Example 1B.

EXAMPLES 2A and 2B

Sunscreen lotion according to the present invention containing different amounts of PARSOL Hydro and UNIVUL N-539 (octocrylene) as shown in the following table:

EXAMPLE 2A

| ingredients in % w/w | 2A a | 2A b | 2A c | 2A d |
|---|---|---|---|---|
| 1 PARSOL 1789 | 2.5 | 2.5 | 2.5 | 2.5 |
| 2 Glyceryl mono myristate | 4.0 | 4.0 | 4.0 | 4.0 |
| 3 CETIOL LC | 2.0 | 2.0 | 2.0 | 2.0 |
| 4 GANEX V 220 | 2.0 | 2.0 | 2.0 | 2.0 |
| 5 Cetylalcohol | 2.0 | 2.0 | 2.0 | 2.0 |
| 6 MIGLYOL 812 N | 10.0 | 10.0 | 10.0 | 10.0 |
| 7 BHT | 0.1 | 0.1 | 0.1 | 0.1 |
| 8 PHENONIP | 0.6 | 0.6 | 0.6 | 0.6 |
| 9 UNIVUL N-539 | 5.0 | 8.0 | 5.0 | 8.0 |
| 10 LANETTE O | 5.0 | 5.0 | 5.0 | 5.0 |
| 11 CUTINA E 24 | 4.0 | 4.0 | 4.0 | 4.0 |
| 12 PARSOL Hydro | 8.0 | 8.0 | 4.0 | 4.0 |
| 13 Propylene glycol | 10.0 | 10.0 | 10.0 | 10.0 |
| 14 EDTA | 0.1 | 0.1 | 0.1 | 0.1 |
| 15 CARBOPOL 981 (1% sol) | 10.0 | 10.0 | 10.0 | 10.0 |
| 16 Demineralised water qs | 34.7 | 31.7 | 38.7 | 35.7 |
| 17 Diethanolamine qs to pH | 7 | 7 | 7 | 7 | procedure:

The ingredients 1 to 11 are heated to 85° C. while stirring. When homogeneous ingredients 12 to 16, preheated to 75° C. are added while mixing. The mixture is cooled to 40° C. The pH-value is corrected to 7 with diethanol-amine. The water loss was compensated and the mixture was cooled to ambient temperature under stirring.

EXAMPLE 2B

| ingredients in % w/w | 2B a | 2B b | 2B c | 2B d |
|---|---|---|---|---|
| 1 PARSOL 1789 | 2.5 | 2.5 | 2.5 | 2.5 |
| 2 UNIVUL N-539 | 8.0 | 5.0 | 8.0 | 5.0 |
| 3 Arlamol E | 5.0 | 5.0 | 5.0 | 5.0 |
| 4 Arlamol HD | 5.0 | 5.0 | 5.0 | 5.0 |
| 5 Brij 72 | 3.0 | 3.0 | 3.0 | 3.0 |
| 6 Brij 721 | 2.0 | 2.0 | 2.0 | 2.0 |
| 7 Arlacel P135 | 0.5 | 0.5 | 0.5 | 0.5 |
| 8 Lanette O | 5.0 | 5.0 | 5.0 | 5.0 |
| 9 Stearic Acid | 1.5 | 1.5 | 1.5 | 1.5 |
| 10 Silbione Oil 70047V20 | 1.0 | 1.0 | 1.0 | 1.0 |
| 11 BHT | 0.1 | 0.1 | 0.1 | 0.1 |
| 12 Phenonip | 0.6 | 0.6 | 0.6 | 0.6 |
| 13 PARSOL Hydro | 8.0 | 8.0 | 4.0 | 4.0 |
| 14 Keltrol 1% sol'n | 12.0 | 12.0 | 12.0 | 12.0 |
| 15 Propylene Glycol | 4.0 | 4.0 | 4.0 | 4.0 |
| 16 Umordan P | 1.0 | 1.0 | 1.0 | 1.0 |
| 17 Deionized Water qsp | 100 | 100 | 100 | 100 |

Procedure: The ingredients 1 to 12 were heated to 85° C. while stirring. When homogeneous ingredients 13 to 17 were preheated to 75° C. and added to the organic phase. The emulsion is then cooled to 40° C. The water loss was compensated and the mixture was cooled to the ambient temperature under stirring.

EXAMPLES 3A and 3B

Sunscreen lotion according to the present invention containing different amounts of potassium salt of p-methoxycinnamic acid and UNIVUL N-539 (octocrylene) as shown in the following table:

| ingredients in % w/w | 3A a | 3A b | 3A c | 3A d |
|---|---|---|---|---|
| 1 PARSOL 1789 | 2.5 | 2.5 | 2.5 | 2.5 |
| 2 Glyceryl mono myristate | 4.0 | 4.0 | 4.0 | 4.0 |
| 3 CETIOL LC | 2.0 | 2.0 | 2.0 | 2.0 |
| 4 GANEX V 220 | 2.0 | 2.0 | 2.0 | 2.0 |
| 5 Cetylalcohol | 2.0 | 2.0 | 2.0 | 2.0 |
| 6 MIGLYOL 812 N | 10.0 | 10.0 | 10.0 | 10.0 |
| 7 BHT | 0.1 | 0.1 | 0.1 | 0.1 |
| 8 PHENONIP | 0.6 | 0.6 | 0.6 | 0.6 |
| 9 UNIVUL N-539 | 5.0 | 8.0 | 5.0 | 8.0 |
| 10 LANETTE O | 5.0 | 5.0 | 5.0 | 5.0 |
| 11 CUTINA E 24 | 4.0 | 4.0 | 4.0 | 4.0 |
| 12 potassium salt of p-methoxycinnamic acid | 8.0 | 8.0 | 4.0 | 4.0 |
| 13 Propylene glycol | 10.0 | 10.0 | 10.0 | 10.0 |
| 14 EDTA | 0.1 | 0.1 | 0.1 | 0.1 |
| 15 CARBOPOL 981 (1% sol) | 10.0 | 10.0 | 10.0 | 10.0 |
| 16 Demineralised water qs | 34.7 | 31.7 | 38.7 | 35.7 |
| 17 KOH qs to pH | 7 | 7 | 7 | 7 |

Procedure: according to Example 2A

EXAMPLE 3B

| ingredients in % w/w | 3B a | 3B b | 3B c | 3B d |
|---|---|---|---|---|
| 1 PARSOL 1789 | 2.5 | 2.5 | 2.5 | 2.5 |
| 2 UNIVUL N-539 | 8.0 | 5.0 | 8.0 | 5.0 |
| 3 Arlamol E | 5.0 | 5.0 | 5.0 | 5.0 |
| 4 Arlamol HD | 5.0 | 5.0 | 5.0 | 5.0 |
| 5 Brij 72 | 3.0 | 3.0 | 3.0 | 3.0 |
| 6 Brij 721 | 2.0 | 2.0 | 2.0 | 2.0 |
| 7 Arlacel P135 | 0.5 | 0.5 | 0.5 | 0.5 |
| 8 Lanette O | 5.0 | 5.0 | 5.0 | 5.0 |
| 9 Stearic Acid | 1.5 | 1.5 | 1.5 | 1.5 |
| 10 Silbione Oil 70047V20 | 1.0 | 1.0 | 1.0 | 1.0 |
| 11 BHT | 0.1 | 0.1 | 0.1 | 0.1 |
| 12 Phenonip | 0.6 | 0.6 | 0.6 | 0.6 |
| 13 Potassium salt of p-methoxycinnamic acid | 8.0 | 8.0 | 4.0 | 4.0 |
| 14 Keltrol 1% sol'n | 12.0 | 12.0 | 12.0 | 12.0 |
| 15 Propylene Glycol | 4.0 | 4.0 | 4.0 | 4.0 |
| 16 Umordan P | 1.0 | 1.0 | 1.0 | 1.0 |
| 17 Deionized Water qsp | 100 | 100 | 100 | 100 |

Procedure: according to Example 2B

EXAMPLE 4

Sunscreen lotion according to the present invention containing different amounts of sodium salt of p-methoxycinnamic acid and UNIVUL N-539 (octocrylene) as shown in the following table:

| ingredients in % w/w | 4 a | 4 b |
|---|---|---|
| 1 PARSOL 1789 | 2.5 | 2.5 |
| 2 Glyceryl mono myristate | 4.0 | 4.0 |
| 3 CETIOL LC | 2.0 | 2.0 |
| 4 GANEX V 220 | 2.0 | 2.0 |
| 5 Cetylalcohol | 2.0 | 2.0 |
| 6 MIGLYOL 812 N | 10.0 | 10.0 |
| 7 BHT | 0.1 | 0.1 |
| 8 PHENONIP | 0.6 | 0.6 |
| 9 UNIVUL N-539 | 5.0 | 8.0 |
| 10 LANETTE O | 5.0 | 5.0 |
| 11 CUTINA E 24 | 4.0 | 4.0 |
| 12 Sodium salt of p-methoxycinnamic acid | 4.0 | 4.0 |
| 13 Propylene glycol | 10.0 | 10.0 |

-continued

| | ingredients in % w/w | 4 a | 4 b |
|---|---|---|---|
| 14 | EDTA | 0.1 | 0.1 |
| 15 | CARBOPOL 981 (1% sol) | 10.0 | 10.0 |
| 16 | Demineralised water qs | 38.7 | 35.7 |
| 17 | NaOH qs to pH | 7 | 7 |

Procedure: according to Example 2A

EXAMPLE 5

Sunscreen emulsion according to the present invention containing different amounts of monoethanolamine salt of p-methoxycinnamic acid and octocrylene (UNIVUL N-539) as shown in the following table:

| | ingredients in % W/W | 5 a | 5 b | 5 c | 5 d |
|---|---|---|---|---|---|
| 1 | PARSOL 1789 | 2.5 | 2.5 | 2.5 | 2.5 |
| 2 | UNIVUL N-539 | 8.0 | 5.0 | 8.0 | 5.0 |
| 3 | Arlamol E | 5.0 | 5.0 | 5.0 | 5.0 |
| 4 | Arlamol HD | 5.0 | 5.0 | 5.0 | 5.0 |
| 5 | Brij 72 | 3.0 | 3.0 | 3.0 | 3.0 |
| 6 | Brij 721 | 2.0 | 2.0 | 2.0 | 2.0 |
| 7 | Arlacel P135 | 0.5 | 0.5 | 0.5 | 0.5 |
| 8 | Lanette O | 5.0 | 5.0 | 5.0 | 5.0 |
| 9 | Stearic Acid | 1.5 | 1.5 | 1.5 | 1.5 |
| 10 | Silbione Oil 70047V20 | 1.0 | 1.0 | 1.0 | 1.0 |
| 11 | BHT | 0.1 | 0.1 | 0.1 | 0.1 |
| 12 | Phenonip | 0.6 | 0.6 | 0.6 | 0.6 |
| 13 | monoethanolamine salt of p-methoxycinnamic acid | 8.0 | 8.0 | 4.0 | 4.0 |
| 14 | Keltrol 1% sol'n | 12.0 | 12.0 | 12.0 | 12.0 |
| 15 | Propylene Glycol | 4.0 | 4.0 | 4.0 | 4.0 |
| 16 | Umordan P | 1.0 | 1.0 | 1.0 | 1.0 |
| 17 | Deionized Water qsp | 100 | 100 | 100 | 100 |

Procedure: according to Example 2B

EXAMPLE 6

Sunscreen lotion according to the present invention containing different amounts of ammonium salt of p-methoxycinnamic acid and UNIVUL N-539 (octocrylene) as shown in the following table:

| | ingredients in % w/w | 6 a | 6 b |
|---|---|---|---|
| 1 | PARSOL 1789 | 2.5 | 2.5 |
| 2 | Glyceryl mono myristate | 4.0 | 4.0 |
| 3 | CETIOL LC | 2.0 | 2.0 |
| 4 | GANEX V 220 | 2.0 | 2.0 |
| 5 | Cetylalcohol | 2.0 | 2.0 |
| 6 | MIGLYOL 812 N | 10.0 | 10.0 |
| 7 | BHT | 0.1 | 0.1 |
| 8 | PHENONIP | 0.6 | 0.6 |
| 9 | UNIVUL N-539 | 5.0 | 8.0 |
| 10 | LANETTE O | 5.0 | 5.0 |
| 11 | CUTINA E 24 | 4.0 | 4.0 |
| 12 | Ammonium salt of p-methoxycinnamic acid | 4.0 | 4.0 |
| 13 | Propylene glycol | 10.0 | 10.0 |
| 14 | EDTA | 0.1 | 0.1 |
| 15 | CARBOPOL 981 (1% sol) | 10.0 | 10.0 |
| 16 | Demineralised water qs | 38.7 | 35.7 |
| 17 | NH$_4$OH qs to pH | 7 | 7 |

Procedure: according to Example 2A

EXAMPLE 7

Sunscreen emulsion according to the present invention containing different amounts of triethanolamine salt of p-methoxycinnamic acid and octocrylene (UNIVUL N-539) as shown in the following table:

| | ingredients in % W/W | 7 a | 7 b | 7 c | 7 d |
|---|---|---|---|---|---|
| 1 | PARSOL 1789 | 2.5 | 2.5 | 2.5 | 2.5 |
| 2 | UNIVUL N-539 | 8.0 | 5.0 | 8.0 | 5.0 |
| 3 | Arlamol E | 5.0 | 5.0 | 5.0 | 5.0 |
| 4 | Arlamol HD | 5.0 | 5.0 | 5.0 | 5.0 |
| 5 | Brij 72 | 3.0 | 3.0 | 3.0 | 3.0 |
| 6 | Brij 721 | 2.0 | 2.0 | 2.0 | 2.0 |
| 7 | Arlacel P135 | 0.5 | 0.5 | 0.5 | 0.5 |
| 8 | Lanette O | 5.0 | 5.0 | 5.0 | 5.0 |
| 9 | Stearic Acid | 1.5 | 1.5 | 1.5 | 1.5 |
| 10 | Silbione Oil 70047V20 | 1.0 | 1.0 | 1.0 | 1.0 |
| 11 | BHT | 0.1 | 0.1 | 0.1 | 0.1 |
| 12 | Phenonip | 0.6 | 0.6 | 0.6 | 0.6 |
| 13 | triethanolamine salt of p-methoxycinnamic acid | 8.0 | 8.0 | 4.0 | 4.0 |
| 14 | Keltrol 1% sol'n | 12.0 | 12.0 | 12.0 | 12.0 |
| 15 | Propylene Glycol | 4.0 | 4.0 | 4.0 | 4.0 |
| 16 | Umordan P | 1.0 | 1.0 | 1.0 | 1.0 |
| 17 | Deionized Water qsp | 100 | 100 | 100 | 100 |

Procedure: according to Example 2B

EXAMPLES 8A and 8B

Sunscreen lotion containing different amounts of PARSOL Hydro or salts of p-methoxycinnamic acid and UNIVUL N-539 whereby the mole ratio of UNIVUL N539 to PARSOL 1789 is less than 0.8 as shown in the tables below.

EXAMPLE 8A

| | ingredients in % w/w | 8A a | 8A b | 8A c | 8A d | 8A e | 8A f |
|---|---|---|---|---|---|---|---|
| 1 | PARSOL 1789 | 2.5 | 2.5 | 2.5 | 2.5 | 2.5 | 2.5 |
| 2 | Glyceryl mono myristate | 4.0 | 4.0 | 4.0 | 4.0 | 4.0 | 4.0 |
| 3 | CETIOL LC | 2.0 | 2.0 | 2.0 | 2.0 | 2.0 | 2.0 |
| 4 | GANEX V 220 | 2.0 | 2.0 | 2.0 | 2.0 | 2.0 | 2.0 |
| 5 | Cetylalcohol | 2.0 | 2.0 | 2.0 | 2.0 | 2.0 | 2.0 |
| 6 | MIGLYOL 812 N | 10.0 | 10.0 | 10.0 | 10.0 | 10 | 10 |
| 7 | BHT | 0.1 | 0.1 | 0.1 | 0.1 | 0.1 | 0.1 |
| 8 | PHENONIP | 0.6 | 0.6 | 0.6 | 0.6 | 0.6 | 0.6 |
| 9 | UNIVUL N-539 | 2.0 | 2.0 | 2.0 | 2.0 | 2.0 | 2.0 |
| 10 | LANETTE O | 5.0 | 5.0 | 5.0 | 5.0 | 5.0 | 5.0 |
| 11 | CUTINA E24 | 4.0 | 4.0 | 4.0 | 4.0 | 4.0 | 4.0 |
| 12 | PARSOL Hydro, or potassium salt of p-Methoxycinnamic acid sodium salt of p-Methoxycinnamic acid ammonium salt of p-Methoxycinnamic acid | 8.0 | 4.0 | 8.0 | 4.0 | 4.0 | 4.0 |
| 13 | Propylene glycol | 10.0 | 10.0 | 10.0 | 10.0 | 10.0 | 10.0 |
| 14 | EDTA | 0.1 | 0.1 | 0.1 | 0.1 | 0.1 | 0.1 |
| 15 | CARBOPOL 981 (1% sol) | 10.0 | 10.0 | 10.0 | 10.0 | 10.0 | 10.0 |
| 16 | demineralised water qs | 37.7 | 41.7 | 29.7 | 33.7 | 33.7 | 33.7 |
| 17 | KOH or NaOH or NH$_4$OH qs to pH | 7 | 7 | 7 | 7 | 7 | 7 |

Procedure: according to Example 2A

EXAMPLE 8B

| ingredients in % W/W | 8B a | 8B b | 8B c | 8B d | 8B e | 8B f | 8B g | 8B h |
|---|---|---|---|---|---|---|---|---|
| 1 PARSOL 1789 | 2.5 | 2.5 | 2.5 | 2.5 | 2.5 | 2.5 | 2.5 | 2.5 |
| 2 UNIVUL N-539 | 2.0 | 2.0 | 2.0 | 2.0 | 2.0 | 2.0 | 2.0 | 2.0 |
| 3 Arlamol E | 5.0 | 5.0 | 5.0 | 5.0 | 5.0 | 5.0 | 5.0 | 5.0 |
| 4 Arlamol HD | 5.0 | 5.0 | 5.0 | 5.0 | 5.0 | 5.0 | 5.0 | 5.0 |
| 5 Brij 72 | 3.0 | 3.0 | 3.0 | 3.0 | 3.0 | 3.0 | 3.0 | 3.0 |
| 6 Brij 721 | 2.0 | 2.0 | 2.0 | 2.0 | 2.0 | 2.0 | 2.0 | 2.0 |
| 7 Arlacel P135 | 0.5 | 0.5 | 0.5 | 0.5 | 0.5 | 0.5 | 0.5 | 0.5 |
| 8 Lanette O | 5.0 | 5.0 | 5.0 | 5.0 | 5.0 | 5.0 | 5.0 | 5.0 |
| 9 Stearic Acid | 1.5 | 1.5 | 1.5 | 1.5 | 1.5 | 1.5 | 1.5 | 1.5 |
| 10 Silbione Oil 70047V20 | 1.0 | 1.0 | 1.0 | 1.0 | 1.0 | 1.0 | 1.0 | 1.0 |
| 11 BHT | 0.1 | 0.1 | 0.1 | 0.1 | 0.1 | 0.1 | 0.1 | 0.1 |
| 12 Phenonip | 0.6 | 0.6 | 0.6 | 0.6 | 0.6 | 0.6 | 0.6 | 0.6 |
| 13 PARSOL Hydro or | 8.0 | 4.0 | | | | | | |
| 13 triethanolamine salt of p-methoxycinnamic acid | | | 8.0 | 4.0 | | | | |
| 13 monoethanolamine salt of p-methoxycinnamic acid | | | | | 8.0 | 4.0 | | |
| 13 Potassium salt of p-methoxycimmamic acid | | | | | | | 8.0 | 4.0 |
| 14 Ketrol 1% sol'n | 12.0 | 12.0 | 12.0 | 12.0 | 12.0 | 12.0 | 12.0 | 12.0 |
| 15 Propylene Glycol | 4.0 | 4.0 | 4.0 | 4.0 | 4.0 | 4.0 | 4.0 | 4.0 |
| 16 Umordan P | 1.0 | 1.0 | 1.0 | 1.0 | 1.0 | 1.0 | 1.0 | 1.0 |
| 17 Deionized Water | 100 | 100 | 100 | 100 | 100 | 100 | 100 | 100 |

Procedure: according to Example 2B

EXAMPLES 9A and 9B

Sunscreen lotion according to the present invention containing different amounts of PARSOL Hydro and PARSOL 5000 as shown in the tables below.

EXAMPLE 9A

| ingredients in % w/w | 9A a | 9Ab |
|---|---|---|
| 1 PARSOL 1789 | 2.5 | 2.5 |
| 2 Glyceryl mono myristate | 4.0 | 4.0 |
| 3 CETIOL LC | 2.0 | 2.0 |
| 4 GANEX V 220 | 2.0 | 2.0 |
| 5 Cetylalcohol | 2.0 | 2.0 |
| 6 MIGLYOL 812 N | 10.0 | 10.0 |
| 7 BHT | 0.1 | 0.1 |
| 8 PHENONIP | 0.6 | 0.6 |
| 9 PARSOL 5000 | 8.0 | 8.0 |
| 10 LANETTE O | 5.0 | 5.0 |
| 11 CUTINA E 24 | 4.0 | 4.0 |
| 12 PARSOL Hydro | 8.0 | 4.0 |
| 13 Propylene glycol | 10.0 | 10.0 |
| 14 EDTA | 0.1 | 0.1 |
| 15 CARBOPOL 981 (1% sol) | 10.0 | 10.0 |
| 16 Demineralised water qs | 34.7 | 31.7 |
| 17 Diethanolamine qs to pH | 7 | 7 |

Procedure: according to Example 2A

EXAMPLE 9B

| ingredients in % W/W | 9B a | 9B b |
|---|---|---|
| 1 PARSOL 1789 | 2.5 | 2.5 |
| 2 PARSOL 5000 | 8.0 | 8.0 |
| 3 Arlamol E | 5.0 | 5.0 |
| 4 Arlamol HD | 5.0 | 5.0 |
| 5 Brij 72 | 3.0 | 3.0 |
| 6 Brij 721 | 2.0 | 2.0 |
| 7 Arlacel P135 | 0.5 | 0.5 |
| 8 Lanette 0 | 5.0 | 5.0 |
| 9 Stearic Acid | 1.5 | 1.5 |
| 10 Silbione Oil 70047V20 | 1.0 | 1.0 |
| 11 BHT | 0.1 | 0.1 |
| 12 Phenonip | 0.6 | 0.6 |
| 13 PARSOL hydro | 8.0 | 4.0 |
| 14 Keltrol 1% sol'n | 12.0 | 12.0 |
| 15 Propylene Glycol | 4.0 | 4.0 |
| 16 Umordan P | 1.0 | 1.0 |
| 17 Deionized Water qsp | 100 | 100 |

Procedure: according to Example 2B

EXAMPLES 10A, 10B and 10C

Sunscreen lotion according to the present invention containing different amounts of potassium salt of p-methoxycinnamic acid and PARSOL 5000 as shown in the following tables:

EXAMPLE 10A

| ingredients in % w/w | 10Aa | 10Ab |
|---|---|---|
| 1 PARSOL 1789 | 2.5 | 2.5 |
| 2 Glyceryl mono myristate | 4.0 | 4.0 |
| 3 CETIOL LC | 2.0 | 2.0 |
| 4 GANEX V 220 | 2.0 | 2.0 |
| 5 Cetylalcohol | 2.0 | 2.0 |
| 6 MIGLYOL 812 N | 10.0 | 10.0 |
| 7 BHT | 0.1 | 0.1 |
| 8 PHENONIP | 0.6 | 0.6 |

-continued

| ingredients in % w/w | 10Aa | 10Ab |
| --- | --- | --- |
| 9 PARSOL 5000 | 8.0 | 8.0 |
| 10 LANETTE O | 5.0 | 5.0 |
| 11 CUTINA E 24 | 4.0 | 4.0 |
| 12 potassium salt of p-methoxycinnamic acid | 8.0 | 4.0 |
| 13 Propylene glycol | 10.0 | 10.0 |
| 14 EDTA | 0.1 | 0.1 |
| 15 CARBOPOL 981 (1% sol) | 10.0 | 10.0 |
| 16 Demineralised water qs | 34.7 | 31.7 |
| 17 KOH qs to pH | 7 | 7 |

Procedure: according to Example 2 A

EXAMPLE 10B

| ingredients in % W/W | 10B a | 10B b |
| --- | --- | --- |
| 1 PARSOL 1789 | 2.5 | 2.5 |
| 2 PARSOL 5000 | 8.0 | 8.0 |
| 3 Arlamol E | 5.0 | 5.0 |
| 4 Arlamol HD | 5.0 | 5.0 |
| 5 Brij 72 | 3.0 | 3.0 |
| 6 Brij 721 | 2.0 | 2.0 |
| 7 Arlacel P135 | 0.5 | 0.5 |
| 8 Lanette O | 5.0 | 5.0 |
| 9 Stearic Acid | 1.5 | 1.5 |
| 10 Silbione Oil 70047V20 | 1.0 | 1.0 |
| 11 BHT | 0.1 | 0.1 |
| 12 Phenonip | 0.6 | 0.6 |
| 13 Potassium salt of p-methoxycinnamic acid | 8.0 | 4.0 |
| 14 Keltrol 1% sol'n | 12.0 | 12.0 |
| 15 Propylene Glycol | 4.0 | 4.0 |
| 16 Umordan P | 1.0 | 1.0 |
| 17 Deionized Water qsp | 100 | 100 |

Procedure: according to Example 2B

EXAMPLE 10C

| ingredients in % w/w | 10Ca | 10Cb | 10Cc | 10Cd |
| --- | --- | --- | --- | --- |
| 1 PARSOL 1789 | 2.5 | 2.5 | 2.5 | 2.5 |
| 2 Glyceryl mono myristate | 4.0 | 4.0 | 4.0 | 4.0 |
| 3 CETIOL LC | 2.0 | 2.0 | 2.0 | 2.0 |
| 4 GANEX V 220 | 2.0 | 2.0 | 2.0 | 2.0 |
| 5 Cetylalcohol | 2.0 | 2.0 | 2.0 | 2.0 |
| 6 MIGLYOL 812 N | 10.0 | 10.0 | 10.0 | 10.0 |
| 7 BHT | 0.1 | 0.1 | 0.1 | 0.1 |
| 8 PHENONIP | 0.6 | 0.6 | 0.6 | 0.6 |
| 9 PARSOL 5000 | 2.0 | 5.0 | 2.0 | 5.0 |
| 10 LANETTE O | 5.0 | 5.0 | 5.0 | 5.0 |
| 11 CUTINA E 24 | 4.0 | 4.0 | 4.0 | 4.0 |
| 12 potassium salt of p-methoxycinnamic acid | 4.0 | 4.0 | 4.0 | 4.0 |
| 13 Propylene glycol | 10.0 | 10.0 | 10.0 | 10.0 |
| 14 EDTA | 0.1 | 0.1 | 0.1 | 0.1 |
| 15 CARBOPOL 981 (1% sol) | 10.0 | 10.0 | 10.0 | 10.0 |
| 16 Demineralised water qs | 37.7 | 34.7 | 41.7 | 38.7 |
| 17 KOH qs to pH | 7 | 7 | 7 | 7 |

Procedure: according to Example 2A

EXAMPLE 11

Sunscreen emulsion according to the present invention containing different amounts of monoethanolamine salt of p-methoxycinnamic acid and PARSOL 5000 shown in the following table:

| ingredients in % W/W | 11a | 11b |
| --- | --- | --- |
| 1 PARSOL 1789 | 2.5 | 2.5 |
| 2 PARSOL 5000 | 8.0 | 8.0 |
| 3 Arlamol E | 5.0 | 5.0 |
| 4 Arlamol HD | 5.0 | 5.0 |
| 5 Brij 72 | 3.0 | 3.0 |
| 6 Brij 721 | 2.0 | 2.0 |
| 7 Arlacel P135 | 0.5 | 0.5 |
| 8 Lanette O | 5.0 | 5.0 |
| 9 Stearic Acid | 1.5 | 1.5 |
| 10 Silbione Oil 70047V20 | 1.0 | 1.0 |
| 11 BHT | 0.1 | 0.1 |
| 12 Phenonip | 0.6 | 0.6 |
| 13 monoethanolamine salt of p-methoxycinnamic acid | 8.0 | 4.0 |
| 14 Keltrol 1% sol'n | 12.0 | 12.0 |
| 15 Propylene Glycol | 4.0 | 4.0 |
| 16 Umordan P | 1.0 | 1.0 |
| 17 Deionized Water qsp | 100 | 100 |

Procedure: according to Example 2B

EXAMPLE 12

Sunscreen emulsion according to the present invention containing different amounts of triethanolamine salt of p-methoxycinnamic acid and PARSOL 5000 as shown in the following table:

| ingredients in % W/W | 13a | 13b |
| --- | --- | --- |
| 1 PARSOL 1789 | 2.5 | 2.5 |
| 2 PARSOL 5000 | 8.0 | 8.0 |
| 3 Arlamol E | 5.0 | 5.0 |
| 4 Arlamol HD | 5.0 | 5.0 |
| 5 Brij 72 | 3.0 | 3.0 |
| 6 Brij 721 | 2.0 | 2.0 |
| 7 Arlacel P135 | 0.5 | 0.5 |
| 8 Lanette O | 5.0 | 5.0 |
| 9 Stearic Acid | 1.5 | 1.5 |
| 10 Silbione Oil 70047V20 | 1.0 | 1.0 |
| 11 BHT | 0.1 | 0.1 |
| 12 Phenonip | 0.6 | 0.6 |
| 13 triethanolamine salt of p-methoxycinnamic acid | 8.0 | 4.0 |
| 14 Keltrol 1% sol'n | 12.0 | 12.0 |
| 15 Propylene Glycol | 4.0 | 4.0 |
| 16 Umordan P | 1.0 | 1.0 |
| 17 Deionized Water qsp | 100 | 100 |

Procedure: according to Example 2B

EXAMPLES 13A, 13B and 13C

Sunscreen lotion according to the present invention containing different amounts of PARSOL HYDRO or salts of p-methoxycinnamic acid and PARSOL 5000, whereby the weight ratio of PARSOL 5000 to PARSOL 1789 is less than 3 shown in the following table:

EXAMPLE 13A

| ingredients in % w/w | 11 a | 11 b | 11 c | 11 d |
| --- | --- | --- | --- | --- |
| 1 PARSOL 1789 | 2.5 | 2.5 | 2.5 | 2.5 |
| 2 Glyceryl mono myristate | 4.0 | 4.0 | 4.0 | 4.0 |
| 3 CETIOL LC | 2.0 | 2.0 | 2.0 | 2.0 |
| 4 GANEX V 220 | 2.0 | 2.0 | 2.0 | 2.0 |
| 5 Cetylalcohol | 2.0 | 2.0 | 2.0 | 2.0 |
| 6 MIGLYOL 812 N | 10.0 | 10.0 | 10.0 | 10.0 |
| 7 BHT | 0.1 | 0.1 | 0.1 | 0.1 |

-continued

| ingredients in % w/w | 11 a | 11 b | 11 c | 11 d |
|---|---|---|---|---|
| 8 PHENONIP | 0.6 | 0.6 | 0.6 | 0.6 |
| 9 PARSOL 5000 | 2.0 | 5.0 | 2.0 | 5.0 |
| 10 LANETTE O | 5.0 | 5.0 | 5.0 | 5.0 |
| 11 CUTINA E 24 | 4.0 | 4.0 | 4.0 | 4.0 |
| 12 PARSOL HYDRO | 8.0 | 8.0 | 4.0 | 4.0 |
| 13 Propylene glycol | 10.0 | 10.0 | 10.0 | 10.0 |
| 14 EDTA | 0.1 | 0.1 | 0.1 | 0.1 |
| 15 CARBOPOL 981 (1% sol) | 10.0 | 10.0 | 10.0 | 10.0 |
| 16 Demineralised water qs | 37.7 | 34.7 | 41.7 | 38.7 |
| 17 Diethanolamine qs to pH | 7 | 7 | 7 | 7 |

Procedure: according to Example 2A

EXAMPLE 13B

| ingredients in % W/W | 14a | 14b | 14c | 14d | 14e | 14f | 14g | 14h |
|---|---|---|---|---|---|---|---|---|
| 1 PARSOL 1789 | 2.5 | 2.5 | 2.5 | 2.5 | 2.5 | 2.5 | 2.5 | 2.5 |
| 2 PARSOL 5000 | 2.0 | 2.0 | 2.0 | 2.0 | 2.0 | 2.0 | 2.0 | 2.0 |
| 3 Arlamol E | 5.0 | 5.0 | 5.0 | 5.0 | 5.0 | 5.0 | 5.0 | 5.0 |
| 4 Arlamol HD | 5.0 | 5.0 | 5.0 | 5.0 | 5.0 | 5.0 | 5.0 | 5.0 |
| 5 Brij 72 | 3.0 | 3.0 | 3.0 | 3.0 | 3.0 | 3.0 | 3.0 | 3.0 |
| 6 Brij 721 | 2.0 | 2.0 | 2.0 | 2.0 | 2.0 | 2.0 | 2.0 | 2.0 |
| 7 Arlacel P135 | 0.5 | 0.5 | 0.5 | 0.5 | 0.5 | 0.5 | 0.5 | 0.5 |
| 8 Lanette O | 5.0 | 5.0 | 5.0 | 5.0 | 5.0 | 5.0 | 5.0 | 5.0 |
| 9 Stearic Acid | 1.5 | 1.5 | 1.5 | 1.5 | 1.5 | 1.5 | 1.5 | 1.5 |
| 10 Silbione Oil 70047V20 | 1.0 | 1.0 | 1.0 | 1.0 | 1.0 | 1.0 | 1.0 | 1.0 |
| 11 BHT | 0.1 | 0.1 | 0.1 | 0.1 | 0.1 | 0.1 | 0.1 | 0.1 |
| 12 Phenonip | 0.6 | 0.6 | 0.6 | 0.6 | 0.6 | 0.6 | 0.6 | 0.6 |
| 13 PARSOLHydro or | 8.0 | 4.0 | | | | | | |
| 13 triethanolamine salt of p-methoxycinnamic acid | | | 8.0 | 4.0 | | | | |
| 13 monoethanolamine salt of of p-methoxycinnamic acid | | | | | 8.0 | 4.0 | | |
| 13 Potassium salt of p-methoxycinnamic acid | | | | | | | 8.0 | 4.0 |
| 14 Keltrol 1% sol'n | 12.0 | 12.0 | 12.0 | 12.0 | 12.0 | 12.0 | 12.0 | 12.0 |
| 15 Propylene Glycol | 4.0 | 4.0 | 4.0 | 4.0 | 4.0 | 4.0 | 4.0 | 4.0 |
| 16 Umordan P | 1.0 | 1.0 | 1.0 | 1.0 | 1.0 | 1.0 | 1.0 | 1.0 |
| 17 Deionized Water qsp | 100 | 100 | 100 | 100 | 100 | 100 | 100 | 100 |

Procedure: according to Example 2B

EXAMPLE 13C

| ingredients in % W/W | 15a | 15b | 15c | 15d | 15e | 15f | 15g | 15h |
|---|---|---|---|---|---|---|---|---|
| 1 PARSOL 1789 | 2.5 | 2.5 | 2.5 | 2.5 | 2.5 | 2.5 | 2.5 | 2.5 |
| 2 PARSOL 5000 | 5.0 | 5.0 | 5.0 | 5.0 | 5.0 | 5.0 | 5.0 | 5.0 |
| 3 Arlamol E | 5.0 | 5.0 | 5.0 | 5.0 | 5.0 | 5.0 | 5.0 | 5.0 |
| 4 Arlamol HD | 5.0 | 5.0 | 5.0 | 5.0 | 5.0 | 5.0 | 5.0 | 5.0 |
| 5 Brij 72 | 3.0 | 3.0 | 3.0 | 3.0 | 3.0 | 3.0 | 3.0 | 3.0 |
| 6 Brij 721 | 2.0 | 2.0 | 2.0 | 2.0 | 2.0 | 2.0 | 2.0 | 2.0 |
| 7 Arlacel P135 | 0.5 | 0.5 | 0.5 | 0.5 | 0.5 | 0.5 | 0.5 | 0.5 |
| 8 Lanette O | 5.0 | 5.0 | 5.0 | 5.0 | 5.0 | 5.0 | 5.0 | 5.0 |
| 9 Stearic Acid | 1.5 | 1.5 | 1.5 | 1.5 | 1.5 | 1.5 | 1.5 | 1.5 |
| 10 Silbione Oil 70047V20 | 1.0 | 1.0 | 1.0 | 1.0 | 1.0 | 1.0 | 1.0 | 1.0 |
| 11 BHT | 0.1 | 0.1 | 0.1 | 0.1 | 0.1 | 0.1 | 0.1 | 0.1 |
| 12 Phenonip | 0.6 | 0.6 | 0.6 | 0.6 | 0.6 | 0.6 | 0.6 | 0.6 |
| 13 PARSOL hydro or Diethanolamine salt of p-methoxycinnamic acid | 8.0 | 4.0 | | | | | | |
| 13 Potassium salt of p-methoxycinnamic acid | | | 8.0 | 4.0 | | | | |
| 13 monoethanolamine salt of p-methoxycinnamic | | | | | 8.0 | 4.0 | | |

-continued

| ingredients in % W/W | 15a | 15b | 15c | 15d | 15e | 15f | 15g | 15h |
|---|---|---|---|---|---|---|---|---|
| acid | | | | | | | | |
| 13 triethanolamine salt of p-methoxycinnamic acid | | | | | | | 8.0 | 4.0 |
| 14 Keltrol 1% sol'n | 12.0 | 12.0 | 12.0 | 12.0 | 12.0 | 12.0 | 12.0 | 12.0 |
| 15 Propylene Glycol | 4.0 | 4.0 | 4.0 | 4.0 | 4.0 | 4.0 | 4.0 | 4.0 |
| 16 Umordan P | 1.0 | 1.0 | 1.0 | 1.0 | 1.0 | 1.0 | 1.0 | 1.0 |
| 17 Deionized Water | 100 | 100 | 100 | 100 | 100 | 100 | 100 | 100 |

Procedure: according to Example 2B

EXAMPLE 14

The desired stabilisation of the material of UV-A filters is easily established by strictly parallel experiments with the respective UV-A filters, UV-B filters and the stabiliser using an appropriately equipped Xenon lamp as a solar simulator. Irradiated are standard preparations of the investigated products, the resulting sunscreen being spreaded on glass plates. After irradiation, the plates are immersed into a suitable solvent (e.g.in ethanol) and analysed by HPLC. The stabilising effect is directly correlated to the difference in area before and after irradiation.

The following tables I–III show the stabilising effect expressed as percentage of absorbance after 10 MED unit respect to non exposed samples=100% at λmax. %: % remaining PARSOL 1789

TABLE I

| Comparative | | | | | |
|---|---|---|---|---|---|
| Ex. No | % | Ex. No | % | Ex. No | % |
| 1A a | 46 | 1B a | 38 | 1C a | 18 |
| 1A b | 48 | 1B b | 30 | 1C b | 30 |
| 1A c | 54 | 1B c | 18 | 1C c | 32 |
| 1A d | 60 | 1B d | 49 | 1C d | 34 |
| 1A e | 68 | 1B e | 45 | 1C e | 36 |
| 1A f | 69 | 1B f | 28 | 1C f | 43 |

TABLE II

| octocrylene as stabilizer | | | | | | | |
|---|---|---|---|---|---|---|---|
| Ex. No | % | Ex. No | % | Ex. No | % | Ex. No | % |
| 2A a | 83 | 3A a | 85 | 4a | 84 | 8A a | 77 |
| 2A b | 86 | 3A b | 92 | 4b | 87 | 8A b | 80 |
| 2A c | 84 | 3A c | 83 | 5a | 58 | 8A c | 76 |
| 2A d | 88 | 3A d | 90 | 5b | 61 | 8A d | 79 |
| 2B a | 58 | 3B a | 87 | 5c | 71 | 8A e | 75 |
| 2B b | 63 | 3B b | 91 | 5d | 58 | 8A f | 72 |
| 2B c | 70 | 3B c | 89 | 6a | 78 | | |
| 2B d | 73 | 3B d | 86 | 6b | 81 | 8B a | 69 |
| | | | | 7a | 74 | 8B b | 55 |
| | | | | 7b | 73 | 8B c | 58 |
| | | | | 7c | 76 | 8B d | 68 |
| | | | | 7d | 72 | 8B e | 59 |
| | | | | | | 8B f | 51 |
| | | | | | | 8B g | 75 |
| | | | | | | 8B h | 69 |

TABLE III

| PARSOL 5000 as stabilizer | | | |
|---|---|---|---|
| Ex. No | % | Ex. No | % |
| 9A a | 85 | 13A a | 80 |
| 9A b | 86 | 13A b | 83 |
| 9B a | 60 | 13A c | 81 |
| 9B b | 71 | 13A d | 86 |
| 10A a | 86 | 13B a | 50 |
| 10A b | 86 | 13B b | 62 |
| 10B a | 80 | 13B c | 63 |
| 10B b | 89 | 13B d | 65 |
| 10C a | 78 | 13B e | 55 |
| 10C b | 87 | 13B f | 51 |
| 10C c | 79 | 13B g | 65 |
| 10C d | 84 | 13B h | 65 |
| 11a | 50 | 13C a | 52 |
| 11b | 57 | 13C b | 62 |
| 12a | 70 | 13C c | 79 |
| 12b | 74 | 13C d | 78 |
| | | 13C e | 57 |
| | | 13C f | 51 |
| | | 13C g | 62 |
| | | 13C h | 51 |

We claim:

1. A photostable, cosmetic light screening composition comprising, in a cosmetically acceptable vehicle containing at least one fatty phase,
    a) from about 0.5 to about 5 wt % of a dibenzoylmethane derivative;
    b) from about 0.5 to about 12 wt % of a 3,3-diphenylacrylate derivative or a benzylidene camphor derivative; and
    c) from about 1 to 15 wt % of a water-soluble p-methoxycinnamate derivative.

2. The light screening composition according to claim 1, wherein the dibenzoylmethane derivative is present in an amount of from about 0.5 to about 3 wt %.

3. The light screening composition according to claim 1, wherein the 3,3-diphenylacrylate- or benzylidene camphor derivative is present in an amount of from about 0.5 to about 10 wt %.

4. The light screening composition according to claim 1, wherein the water-soluble p-methoxycinnamate derivative is present in an amount of from about 1 to about 10 wt %.

5. The light screening composition according to claim 1, wherein the dibenzoylmethane derivative is selected from 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane and 2,6-dimethyl-4-tert-butyl-4'-methoxy-dibenzoylmethane.

6. The light screening composition according to claim 5, wherein the dibenzoylmethane derivative is 4-tert.-butyl-4'-methoxydibenzoylmethane.

7. The light screening composition according to claim 1, wherein the 3,3-diphenylacrylate derivative is selected from 2-ethylhexyl-2-cyano-3,3-diphenylacrylate (octocrylene) and 2-ethyl-2-cyano-3,3-diphenylacrylate (etocrylene).

8. The light screening composition according to claim 7, wherein the 3,3-diphenylacrylate derivative is 2-ethylhexyl-2-cyano-3,3-diphenylacrylate (octocrylene).

9. The light screening composition according to claim 1, wherein the benzylidene camphor derivative is p-methylbenzylidene camphor.

10. The light screening composition according to claim 1, wherein the water-soluble p-methoxycinnamate derivative is selected from ammonium- p-methoxycinnamate, sodium-p-methoxycinnamate, potassium-p-methoxycinnamate, salts of primary, secondary or tertiary amines of p-methoxycinnamic acid, aminomethyl-propanol salt of p-methoxycinnamic acid, and morpholine salt of p-methoxycinnamic acid.

11. The light screening composition according to claim 10, wherein the water-soluble p-methoxycinnamate derivative is selected from the mono-, di-, or triethanolamine salt of p-methoxycinnamic acid.

12. The light screening composition according to claim 1, wherein the mole ratio of the 3,3-diphenylacrylate derivative to the dibenzoylmethane derivative is less than 0.8.

13. The light screening composition according to claim 9, wherein the weight ratio of p-methylbenzylidene camphor to the dibenzoylmethane derivative is less than 3.

14. The light screening composition according to claim 1, which is in the form of an oil, a lotion, a cream, a milk, a gel, a solid stick, an aerosol, a spray, a foam, a powder, a shampoo, a hair conditioner, a lacquer or a make-up.

15. A photostable, cosmetic light screening composition comprising, in a cosmetically acceptable vehicle containing at least one fatty phase,
   a) from about 0.5 to about 5 wt % of 4-tert.-butyl-4'-methoxydibenzoylmethane;
   b) from about 0.5 to about 12 wt % of 2-ethylhexyl-2-cyano-3,3-diphenylacrylate; and
   c) from about 1 to about 15 wt % of mono-, di-, or triethanolamine salt of p-methoxy-cinnamic acid.

16. The light screening composition according to claim 15, wherein the mole ratio of 2-ethylhexyl-2-cyano-3,3-diphenylacrylate to of 4-tert.-butyl-4'-methoxydibenzoylmethane is less than 0.8.

17. The light screening composition according to claim 15, which is in the form of an oil, a lotion, a cream, a milk, a gel, a solid stick, an aerosol, a spray, a foam, a powder, a shampoo, a hair conditioner, a lacquer or a make-up.

18. A photostable, cosmetic light screening composition comprising, in a cosmetically acceptable vehicle containing at least one fatty phase,
   a) from about 0.5 to about 5 wt % of 4-tert.-butyl-4'-methoxydibenzoylmethane;
   b) from about 0.5 to about 12 wt % of p-methylbenzylidene camphor; and
   c) from about 1 to about 15 wt % of mono-, di-, or triethanolamine salt of p-methoxycinnamic acid.

19. The light screening composition according to claim 18, wherein the weight ratio of p-methylbenzylidene camphor to 4-tert.-butyl-4'-methoxydibenzoylmethane is less than 3.

20. The light screening composition according to claim 19, which is in the form of an oil, a lotion, a cream, a milk, a gel, a solid stick, an aerosol, a spray, a foam, a powder, a shampoo, a hair conditioner, a lacquer or a make-up.

\* \* \* \* \*